United States Patent [19]

Reichmann et al.

[11] 4,195,031

[45] Mar. 25, 1980

[54] PROCESS FOR THE CONTINUOUS PRODUCTION OF MONOISOCYANATES

[75] Inventors: Wolfgang Reichmann, Duesseldorf; Klaus König, Leverkusen; Johannes Koster, Dormagen, all of Fed. Rep. of Germany

[73] Assignee: Bayer Aktiengesellschaft, Leverkusen, Fed. Rep. of Germany

[21] Appl. No.: 965,648

[22] Filed: Dec. 20, 1978

[30] Foreign Application Priority Data

Dec. 21, 1977 [DE] Fed. Rep. of Germany ....... 2756928

[51] Int. Cl.$^2$ .......................................... C07C 118/00
[52] U.S. Cl. ......................... 260/453 P; 260/453 PH
[58] Field of Search .................................... 260/453 P

[56] References Cited

U.S. PATENT DOCUMENTS

| | | | |
|---|---|---|---|
| 2,409,712 | 10/1946 | Schweitzer | 260/453 P |
| 3,076,007 | 1/1963 | Barclay, Jr. et al. | 260/453 P |
| 3,366,662 | 1/1968 | Kober et al. | 260/453 P |
| 3,734,941 | 5/1973 | Sydor | 260/453 P |
| 3,919,279 | 11/1975 | Rosenthal et al. | 260/453 P |
| 3,919,280 | 11/1975 | Rosenthal et al. | 260/453 P |
| 3,962,302 | 6/1976 | Rosenthal et al. | 260/453 P |
| 4,003,938 | 1/1977 | Koenig et al. | 260/453 P |

*Primary Examiner*—Dolph H. Torrence
*Attorney, Agent, or Firm*—Gene Harsh; Joseph C. Gil; R. Brent Olson

[57] ABSTRACT

The instant invention relates to an improved process for the continuous production of an aliphatic monoisocyanate from the corresponding N-alkyl carbamic acid aryl ester. More particularly, the invention is directed to a process for the continuous production of monoisocyanates corresponding to the formula

R—NCO in which

R represents an aliphatic hydrocarbon radical containing 1 to 3 carbon atoms comprising thermally decomposing the corresponding N-alkylcarbamic acid aryl esters corresponding to the formula

R—NH—CO—O—R' in which

R has the meaning above and

R' represents a radical of the type obtained by removing the hydroxyl group from a monophenol having a boiling point below 250° C. at normal pressure, and separating the decomposition products by decomposition, further characterized in that (a) a solution of the N-alkylcarbamic acid aryl ester in an organic solvent, which solvent is inert under the reaction conditions and has a boiling point lying at least 20° C. above the boiling point of the monoisocyanate to be formed, is heated to a temperature of from 160° C. to 250° C. at normal pressure or at slightly reduced pressure within the range of 200 to 1013 mbar, thereby resulting in the decomposition of the ester into the corresponding monoisocyanate and the corresponding phenol, as well as the evaporation of the solvent and the decomposition products, and (b) the vapors formed are fed into a distillation column with the monoisocyanate obtained at the head of the column and with the phenol and at least a major portion of the solvent obtained from a side stream or from several side streams.

6 Claims, 4 Drawing Figures

PROCESS FOR THE CONTINUOUS PRODUCTION OF MONOISOCYANATES

BACKGROUND OF THE INVENTION

As is known, isocyanates are produced by the reaction of amines with phosgene. The reaction takes place through formation of the carbamic acid chlorides, which split up into the corresponding isocyanates and hydrogen chloride at elevated temperature. If the boiling point of the isocyanate to be produced lies clearly above the decomposition temperature of the carbamic acid chloride, then the hydrogen chloride formed during decomposition may be readily removed from the reaction vessel, particularly when an inert organic solvent is used. However, if the decomposition temperature of the carbamic acid chloride lies around or above the boiling point of the isocyanate, then the isocyanate is present in the gas evolved and will recombine with the hydrogen chloride to form carbamic acid chloride. Decomposition is accordingly incomplete. The resultant isocyanate is obtained in small yields and is contaminated with carbamic acid chloride. This recombination is particularly troublesome in producing $C_1$ to $C_3$ aliphatic monoisocyanates with the greatest difficulties being in the production of methyl isocyanate.

Several processes for overcoming these difficulties have been described. A large number of these processes involve the splitting of carbamic acid chlorides in the presence of hydrogen chloride acceptors.

It is thus known to produce isocyanates from carbamic acid chlorides in organic solvents in the presence of organic bases, such as tertiary amines, carboxylic acid dialkyl amides as described in German Offenlegungsschrift No. 1,593,554 or tetra-alkyl ureas as described in U.S. Pat. No. 3,644,461. Moreover, the use of water is described in German Auslegeschrift No. 2,156,761, and the use of aqueous solutions or suspensions of inorganic bases is described in British Pat. No. 1,208,862, both of these types of materials being described for the absorption of the hydrogen chloride. Also, olefins are described as hydrogen chloride acceptors, in German Offenlegungsschrift No. 2,210,285.

All of these processes have the serious disadvantage that corrosive organic or inorganic salts or alkyl chlorides are formed as by-products which must be further treated in an expensive manner to avoid environmental pollution. In addition, the use of organic bases involves the risk of secondary reactions which lead to the formation of dimeric and trimeric isocyanates. Additionally, a considerable proportion of the carbamic acid chloride is hydrolyzed to the amine-hydrochloride in the presence of water. In general, high yields are only obtained in the case of the relatively inert, tertiary butyl isocyanate.

It is also known to produce low-boiling aliphatic monoisocyanates by thermal splitting of carbamic acid chlorides in organic solvents, by applying special processing techniques.

According to German Auslegeshcirft No. 1,193,034, the thermal splitting of the carbamic acid chloride is carried out in a reactor provided with a reflux condenser and separating column. Hydrogen chloride escapes through the reflux chamber, and isocyanate, carbamic acid chloride and solvent are retained. The isocyanate formed enters the separating column and may be taken off at the head of the column. The majority of the isocyanate is recycled through a reflux divider so that the hydrogen chloride rising in the column is completely absorbed and returns to the reactor in the form of carbamic acid chloride. When this process is carried out continuously, a portion of the solution with reduced carbamic acid chloride content is generally continuously removed from the reactor, enriched with carbamic acid chloride at another point and recycled to the reactor.

German Offenlegungsschriften Nos. 2,411,441; 2,411,442; 2,422,211 and 2,503,270 are typical of prior attempts to thermally split carbamic acid chlorides requiring the use of specific apparatus.

Although it is possible to produce low-boiling aliphatic monoisocyanates by thermal splitting of carbamic acid chlorides by the processes known and described, serious disadvantages are generally observed:

(1) the separation of hydrogen chloride requires reflux condensers with large cooling surfaces which must operate with coolants, consuming a great deal of energy to ensure that isocyanate and carbamic acid chloride are retained quantitatively;

(2) highly efficient fractionation columns are generally required for separating carbamic acid chloride-free isocyanate from the reaction mixture by distillation, since a high reflux ratio must be maintained;

(3) the processes can only be used if relatively dilute carbamic acid chloride solutions having a concentration of 1 to 30% are used; and (4) when the process is carried out continuously, which is generally necessary for commercial applications, the reaction solution must be circulated several times.

All of these disadvantages necessarily require the reactants (isocyanate, carbamic acid chloride and solvent) to be evaporated, condensed or cooled, and reheated several times in the process, thus giving rise to high energy consumption. A long residence time (and, thus a low space-time yield) and the need for many cycles generally follows from the use of dilute solutions. Because of the long residence time, the yield can even be further reduced by trimerization of the monoisocyanate. The process generally requires high expenditure for measurement and control equipment. A relatively high investment for commercial production necessarily results due to the low space-time yield and the need to use highly efficient fractionation columns.

In addition, it is known to produce isocyanates by thermal splitting of carbamic acid esters (Houben-Weyl, Methoden der org. Chemie; Volume 8, page 126, 1952). In this process, carbamic acid aryl esters are preferably used since they split up into isocyanates under milder conditions than do alkyl esters.

Processes for the production of monoisocyanates, in which both carbamic acid aryl esters and carbamic acid alkyl esters are used, are known and described in the literature.

Thus, the corresponding monoisocyanates may be produced by thermal decomposition from N-alkylcarbamic acid-2-hydroxyethyl esters as described in U.S. Pat. No. 3,076,007 and from N-alkylcarbamic acid-β-naphthylesters as described in German Offenlegungsschrift No. 2,512,514.

In these processes, as in the thermal splitting of carbamic acid chlorides, there is the danger that the cleavage products will recombine to reform the starting materials.

According to the process described in U.S. Pat. No. 3,076,007, recombination is prevented by immediately condensing and chilling the decomposition products. The distillates obtained are then diluted with an inert solvent which is immiscible with water. The ethylene glycol can then be removed by repeated extraction with water. This complicated separation of the decomposition products by extraction is not necessary in the process described in German Offenlegungsschrift No. 2,512,514, since the β-naphthol forming during decomposition does not pass into the gaseous phase under the decomposition conditions due to its high boiling point. However, the thermal stress of the β-naphthol is disadvantageous in this case since it causes the formation of undesirable pyrolysis products. This situation is particularly detrimental when the process is carried out continuously because the reused β-naphthol is enriched with impurities which inevitably interfere in the process for the production of the isocyanates. Another disadvantage of the process is that the separation of the isocyanates is slowed down as the decomposition of the carbamic acid esters progresses so that the increase in concentration of β-naphthol taking place with decomposition shifts the equilibrium between β-naphthol, isocyanate and carbamic acid ester according to the principle of mass action.

An object of the present invention is to provide a process for the continuous production of monoisocyanates in which undesirable recombinations, separation problems and unnecessary thermal stresses on the decomposition products formed by thermal decomposition of N-alkyl carbamic acid aryl esters are avoided.

This object could be achieved by the process according to the invention, which is described below.

DESCRIPTION OF THE INVENTION

Figure 1:
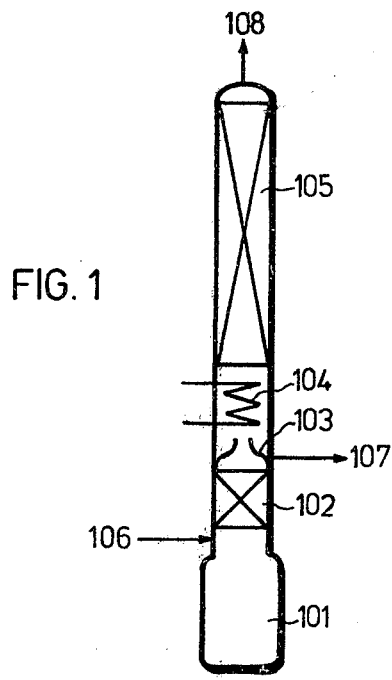
FIGS. 1 through 4 schematically illustrate various embodiments of the invention.

The present invention therefore relates to a process for the continuous production of a monoisocyanate corresponding to the formula

R—NCO in which

R represents an aliphatic hydrocarbon radical containing 1 to 3 carbon atoms which may be olefinically unsaturated, by thermal splitting or decomposition of the corresponding N-alkylcarbamic acid aryl ester corresponding to the formula

R—NH—CO—O—R' in which

R has the meaning above and

R' represents a radical of the type obtained by removal of the hydroxyl group from a monophenol having a boiling point below 250° C. at normal pressure, and separation of the decomposition products by distillation, characterized in that (a) a solution of the N-alkylcarbamic acid ester (which is to be split up) in an organic solvent which is inert under the reaction conditions and has a boiling point at least 20° C. above the boiling point of the monoisocyanate to be formed, is heated at normal pressure or at a slightly reduced pressure within the range of from 200 to 1013 mbar to a temperature in the range of 160° to 250° C. with decomposition of the ester into the corresponding monoisocyanate and the corresponding phenol and evaporation of the solvent and the decomposition products and (b) the vapors produced thereby are fed into a distillation column with the monoisocyanate, optionally together with the portion of the solvent, obtained at the head of the column and with the phenol and at least a major portion of the solvent obtained in a side stream or in several side streams.

The present invention also relates to an embodiment of the invention which is characterized in that the phenol and solvent present in the side stream are reused as a mixture. Alternatively, the phenol and solvent, after separation by fractional distillation, are reused for the production of the solution used as starting material by dissolution of or by reaction with the reaction gases produced during the gaseous phase phosgenation of monoamines (which will correspond to the formula R—NH$_2$, in which R has the meaning given above).

Starting compounds for the process according to the invention include N-alkylcarbamic acid aryl esters corresponding to the formula

R—NH—CO—O—R' in which

R has the meaning already specified above and preferably represents a methyl group and R' has the meaning already specified above and preferably represents a phenyl radical which may be methyl-, ethyl-, methoxy- or ethoxy-substituted. R' most preferably represents an unsubstituted or mono methyl-substituted phenyl radical. Such N-alkylcarbamic acid aryl esters are produced by known methods (Saunders, Frisch, Polyurethanes, Chemistry and Technology, J. Wiley & Sons, New York/London, 1962, Vol. XVI, part I, pages 73ff.). They may be obtained, for example, by reacting alkyl amines with chloroformic aryl esters or diaryl carbonates (Houben Weyl, Methoden der organischen Chemie, 1952, Vol. 8, pages 138 f.).

The esters which are to be used as starting materials in the process of the invention can also be produced in a very simple way by reacting N-aryl carbamic acid chlorides (which are formed by the gaseous phase by phosgenation of the corresponding amines R—NH$_2$) with phenols corresponding to the formula R'—OH (in which R' has the meaning already given).

with elimination of HCl.

The N-alkylcarbamic acid aryl esters to be used as starting materials in the process of the invention are used in the form of their solutions in suitable inert solvents.

Accordingly, the reaction between the reaction gases formed by gaseous phase phosgenation of the amines and the phenol (R'—OH) preferably takes place in the presence of an inert organic solvent. In particular, this reaction occurs (a) either directly by absorption of the reaction gases issuing from the gaseous phase with separation of the hydrogen chloride and excess phosgene with the phenol solution itself, or (b) only after absorption of the reaction gases with an inert organic solvent and if desired, after removal of excess phosgene, wherein both the carbamic acid chloride and the free isocyanate present are converted into the corresponding carbamic acid aryl ester, or, (c) after absorption of the reaction gases according to (b) after distillation of the isocyanate-containing carbamic acid chloride solution in a column with removal of the carbamic acid chloride together with solvent in a side stream of the column, wherein the free isocyanate is separated off at the head of the column and the main portion of the solvent is separated off in the sump of the column.

Variation (c) has two important advantages. Firstly, the monoisocyanate already contained in the absorption solutions of gaseous phase phosgenation is isolated directly and is not reacted unnecessarily with the carbamic acid chloride to form carbamic acid aryl ester. Secondly, removal from the side stream in the distillation process described provides a carbamic acid chloride solution whose concentration is increased in comparison to the relatively low carbamic acid chloride concentrations which the absorption solutions of gaseous phase phosgenation generally have.

The concentrations of the N-alkylcarbamic acid aryl ester solutions used for the process according to the invention generally amount to 5 to 70% by weight, preferably 40 to 60% by weight when using the abovementioned carbamic acid chloride solution.

Suitable phenols R'—OH according to the invention include, for example, phenol itself, o-, m-, or p-cresol, the corresponding isomeric ethyl phenols, the various isomeric xylenols or alkoxy phenols such as o-methoxyphenol or p-ethoxyphenol, and the like. Of course, mixtures of phenols may also be used. Unsubstituted phenol as well as the cresols are preferred. Phenol is particularly preferred.

The solvents to be used in the process according to the invention are those which (a) are inert under the reaction conditions according to the invention and (b) boil at least 20° C., and preferably at least 50° C., above the isocyanates produced according to the invention. The boiling point of the solvents is generally not higher than the boiling point of the phenols but is preferably at least 20° C. below and most preferably at least 50° C. below the boiling point of the phenols used.

Examples of suitable solvents include: n-octane, cyclohexyl chloride, dichloropropane-1,3; isomeric dichlorobutane, toluene, xylene, ethyl benzene, chlorobenzene, dichlorobenzene, acetic acid butyl ester, propionic acid propyl ester, and the like. Of course, mixtures of the solvents mentioned may also be used. Chlorobenzene is the preferred solvent.

The process according to the invention will now be described in more detail with reference to the drawings.

FIG. 1 schematically illustrates a distillation column for carrying out the process of the invention. In this FIGURE, the numerals have the following significance (101) a reaction vessel for the thermal splitting of the ester solution;

(102) the lower section of a packed column mounted on the reaction vessel;

(103) a side stream removal plate;

(104) a temperature-controllable dephlegmator;

(105) the upper section of the packed column;

(106) the inlet for the ester solution to be split up;

(107) removal from the side stream and (108) removal of head product.

When the process according to the invention is carried out, the solution of the N-alkylcarbamic acid aryl ester to be decomposed is fed via 106 to the reaction vessel 101, in which thermal splitting of the carbamic acid ester into isocyanate and phenol takes place at a temperature of 160° to 250° C., preferably 190° to 250° C. and most preferably 200° to 230° C. The decomposition products evaporate together with the solvent immediately after being formed and, via the lower section of a packed column 102, reach the dephlegmator 104 the temperature of which is controlled in such a way that the total quantity of phenol and the majority of the solvent may be condensed and removed from the column at the side stream removal plate 103 in the form of the stream 107. The total quantity of the product of the process is removed from the column via head 108, optionally together with small proportions of solvent and is, if necessary, fed to a purification distillation column.

The apparatus shown in FIG. 1 represents a preferred apparatus for conducting the process of the invention. However, the process of the invention is not restricted to the sole use of the apparatus shown in FIG. 1. Thus, it is also possible to carry out the process according to the invention by removing several side streams, i.e. by using a column which is suitable for the removal of several side streams, wherein the main quantity of the phenol could be removed in a lower side stream and the main quantity of the solvent could be removed in an upper side stream. It is especially appropriate to carry out the process of the invention with removal of several side streams if higher monoisocyanates (ethylisocyanate or propylisocyanates) are to be produced. Due to the higher boiling points of these isocyanates compared to the boiling point of methylisocyanate the whole temperature profile within the column is increased. Due to this higher temperature profile, small amounts of phenol may reach the top of the column together with the isocyanate. In principle this can be avoided by a lower temperature of the dephlegmator which, however, would necessarily increase the amount of isocyanate in the phenol solution (107). Since this amount has to be minimized the temperature of the dephlegmator cannot generally be decreased arbitrarily. It is therefore more advantageous to fix the temperature of the dephlegmator so that the amount of isocyanate in the phenol solution is small. The phenol passing through the dephlegmator is then removed in a second side stream above the dephlegmator together with small amounts of isocyanate and carbamic acid aryl ester as a solution in a part of the solvent and recycled into the apparatus underneath the removal (107) of the first side stream. The relatively high temperature within the column in the case of the production of the higher monoisoyanates has the further consequence that the phenol and the isocyanate may recombine. To prevent such recombination it is therefore advisable to carry out the process at a slightly reduced pressure within the range of from 200 to 1013 mbar.

In addition, it is not absolutely essential to use the dephlegmator shown in FIG. 1 for the partial condensation of the vapors rising in the column. Instead, condensation may also be ensured by another method a carrying off the heat, such as, for example, heat radiation. The only factor which is essential for carrying out the process of the invention is that the total quantity of solvent and of cleavage products is evaporated and that the blocking agent (phenol), in the form of a side stream, and the end product (monoisocyanate), at the head of the column, are removed. In addition, the temperature in the column is generally controlled by removing the main quantity, i.e. more than 50%, preferably at least 75%, of the total quantity of the solvent introduced, in the form of one or more side streams, so that at most up to 50% of the total quantity of the solvent introduced is present in the head product.

Figure 2:
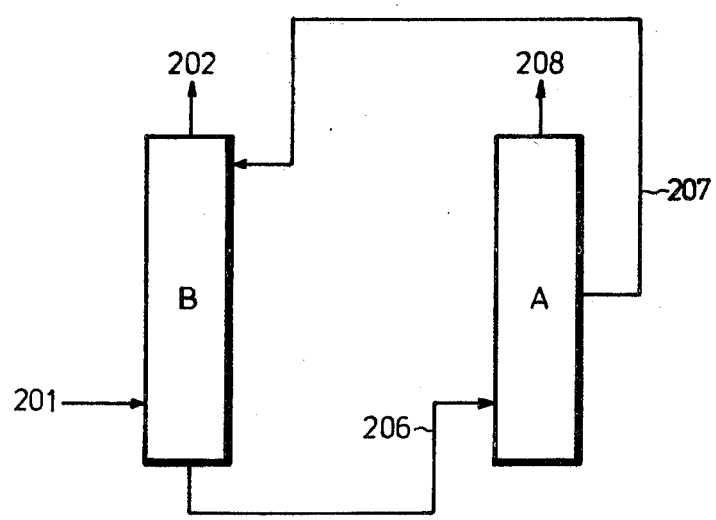
Figure 3:
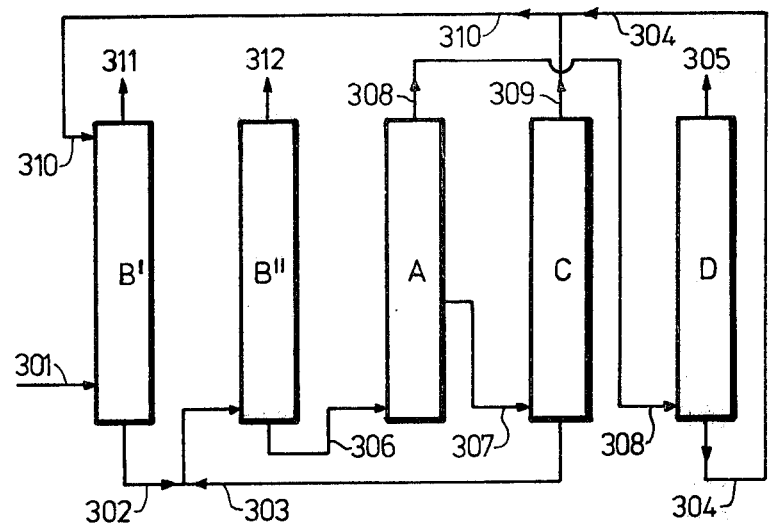
Figure 4:
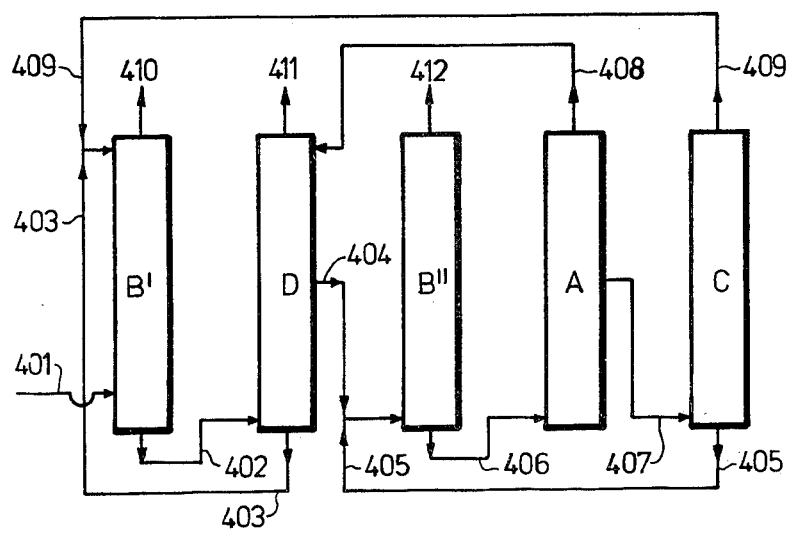

Further embodiments of the process of the invention are illustrated in FIGS. 2 to 4, in which the column shown in detail in FIG. 1 is represented by "A" in each case.

In addition to this column A, FIG. 2 shows a washing column B. When carrying out the process according to the invention in accordance with the embodiment shown in FIG. 2, the reaction gases 201 leaves a gaseous phase phosgenation reactor (not shown), enter the washing column B in which they are combined with a solution of a phenol in an inert solvent 207 and are reacted. The gas stream, optionally cooled in the upper section of column B, is generally combined with the solution 207 at a temperature of from 20° to 150° C. Excess phosgene and hydrogen chloride formed by the reaction between chamber acid chloride and phenol are expelled and removed via 202 by heating the solution formed (bottom of column B). The solution 206 removed from the bottom of column B represents the actual starting material for carrying out the process of the invention. The side stream 207 corresponds to the side stream 107 and represents a solution containing the total quantity of phenol which is recycled into the washing column B without being further worked up. The product of the process is obtained in the form of the stream 208 at the head of the column A. This stream 208 may also consist of a solution of the isocyanate in small amounts of the solvent which solution may be separated in a further distillation column (not shown in the drawing) into pure isocyanate and pure solvent which may be reused in the process of the invention.

The apparatus in FIG. 3 differs from the apparatus in FIG. 2 essentially by the simultaneous use of a washing column B' and a hydrogen chloride separator B" and by subsequent columns C and D in which the over-head product from the main column A or the side stream from the main column A are worked up by distillation.

When carrying out the process according to the invention according to the embodiment shown in FIG. 3, the reaction gases 301 corresponding to 201 from FIG. 2 enter a first column B' in which they are absorbed at 10° to 30° C. with an organic solvent so that hydrogen chloride and phosgene escape via 311 as a result of heating the reaction solution to about 90° C. to 120° C. The phosgene-free reaction solution 302 which contains fractions of free isocyanate in addition to the carbamic acid chloride is then combined with a phenol 303 of a type suitable for the invention and is reacted in the hydrogen chloride separator B" by heating to about 80° to 150° C. with separation of hydrogen chloride 312 to form carbamic acid aryl ester solution 306 which is split up in the main column into a phenol solution 307 and a monoisocyanate solution 308. The phenol solution 307 in column C is split up into pure solvent 309 and concentrated phenol solution 303 (about 80% by weight). The head product 308 fed to column D is split up into pure monoisocyanate 305 and pure solvent 304 in column D. The combined streams 304 and 309 form the solvent stream 310 used in column B'.

The apparatus shown in FIG. 4 differs from the apparatus in FIG. 3 by the arrangement of the distillation column D, used for preparation of the pure product of the process, between column B' and the hydrogen chloride separator B", in which D is not only used for the preparation of the pure product of the process occurring in the main column, but is also used for isolating the monoisocyanate already present in the gaseous phosgenation product. When the process according to the invention is carried out, in accordance with the embodiment shown in FIG. 4, the gaseous phosgenation mixture 401 which is composed essentially of monoisocyanate, carbamic acid chloride, hydrogen chloride and excess phosgene, enters washing column B' in which a solution 402 containing carbamic acid chloride and monoisocyanate is formed by using the solvent streams 403 and 409 and by distilling off the hydrogen chloride already present and excess phosgene 410 at 90° to 120° C. This solution containing monoisocyanate and carbamic acid chloride then enters the distillation column D where it is converted into monoisocyanate 411, pure solvent 403 and a concentrated carbamic acid chloride solution 404. This carbamic acid chloride solution 404 is combined with the concentrated phenol solution 405 and is reacted in the hydrogen chloride separator B" at 80° to 150° C. to form hydrogen chloride 412 and carbamic acid aryl ester solution 406. The solution 406 is decomposed in the main column A as already stated above so that the side stream 407 is separated into pure solvent 409 and concentrated phenol solution 405 as in the embodiment in FIG. 3. The overhead product 408 is introduced into the upper section of column D so that the monoisocyanate contained in 408 is obtained in pure form in the stream 411 while the solvent contained in 408 is taken up in 403 and 404.

The continuous process of the invention has the following advantages over known processes for the production of low-boiling monoisocyanates:

1. The undesirable recombination of the decomposition products during thermal splitting of carbamic acid chlorides into alkyl isocyanates and hydrogen chloride is completely eliminated by converting the carbamic acid chlorides into the carbamic acid aryl esters which are only splitable at elevated temperatures. The hydrogen chloride produced during formation of the carbamic acid aryl esters is completely removed in a simple manner prior to carbamic acid ester cleavage so that the isocyanate yields are not reduced by re-formation of carbamic acid chloride later on in the process. The hydrogen chloride separators B" shown in FIGS. 3 and 4 are preferably simple heatable reaction vessels having reflux condensers mounted on them, through which the hydrogen chloride escapes.

2. The use of the phenols specified according to the invention for the formation of N-alkyl carbamic acid aryl esters allows both of the decomposition products formed during splitting of the carbamic acid esters to be evaporated together with the solvent used. Although both decomposition products are in contact in the gaseous phase, recombination of the decomposition products is almost completely avoided due to the separation process of the invention.

3. The conversion of the phenols according to the invention into the gaseous phase is a valuable cleaning stage with respect to the circulation of the phenol. It eliminates from the start the possibility of any interference in the continuous progress of the process by high-boiling impurities or impurities which cannot evaporate under the reaction conditions. Such impurities remain in the bottom of the carbamic acid ester splitting vessel and can be discharged from there in a simple way, if necessary.

The types of apparatus to be used in the process according to the invention, apart from the features essential to the invention, are those which are conventional in the chemical processing industry and are made of the materials which are generally suitable for use in such reactions.

The aliphatic monoisocyanates which may be produced by the process according to the invention are valuable starting compounds for the manufacture of plant-protecting agents and pharmaceuticals.

EXAMPLES

EXAMPLE 1 (FIGS. 1 and 2)

2.0 kg (64.5 mol) per hour of methylamine and 9 kg (90.9 mol) per hour of phosgene are each preheated to about 180° C. and reacted in a mixing chamber at about 350° C. The reaction gases 201 issuing from the mixing chamber are absorbed in an absorption column at a rate of 17.5 kg per hour of a 40% by weight phenol solution in chlorobenzene, corresponding to 74.4 mol of phenol. The reaction solution formed in the process is freed from hydrogen chloride and excess phosgene 202 by heating to 140° C. The solution 206 of carbamic acid aryl ester produced in process is split up in the vessel A (101 in FIG. 1) at 230° C., with evaporation of the solvent, into gaseous monoisocyanate and gaseous phenol and the decomposition products enter the distillation column arranged above the reaction vessel 101, which distillation column is equipped with a dephlegmator 104 having the temperature adjusted to 70° C. 3.5 kg, corresponding to 96% of the theoretical yield, of pure methyl isocyanate 108 are removed at the head of the column per hour, and the phenol solution 207 removed below the dephlegmator is recirculated to the washing column B.

EXAMPLE 2 (FIGS. 1 and 3)

124 g (4 mol) per hour of methylamine and 495 g (5 mol) per hour of phosgene are preheated separately to about 200° C. and reacted in a reaction tube at about 350° C. The reaction gases 301 formed in the process are absorbed with 2000 g of chlorobenzene 310 per hour so that a reaction solution 302 containing 11.2% by weight of N-methylcarbamic acid chloride and 2.9% by weight of methyl isocyanate is obtained after removing the hydrogen chloride and the excess phosgene 311. This solution 302 is mixed with 564 g per hour of a circulated 80% by weight solution 303 of phenol in chlorobenzene, corresponding to 4.8 mol of phenol. In the process, both the monoisocyanate and the carbamic acid chloride, the latter with separation of hydrogen chloride 312, are converted into carbamic acid phenyl ester by heating to 80° to 140° C. The carbamic acid ester solution 306 formed in the process is split up as in Example 1 at 220° C. into gaseous methyl isocyanate, gaseous phenol and solvent vapor so that 376 g per hour of a 60% by weight solution of methyl isocyanate in chlorobenzene 308 is removed per hour above the dephlegmator 104 regulated to 125° C. at the column head. 2414 g per hour of an 18.5% by weight solution of phenol in chlorobenzene are removed beneath the cooling apparatus as sidestream 107 or 307. The methyl isocyanate solution 108 or 308 is then split up in a subsequent distillation column into 221 g per hour, corresponding to 97% of the theoretical yield, of pure methyl isocyanate 305 and solvent 304. The phenol solution produced as side stream 107 or 307 is concentrated in a separate distillation column by distillation of 1850 g per hour of chlorobenzene 309 to a phenol content of 80% by weight and and is reused. The solvent stream 309 is combined with the solvent stream 304 and is reused as a combined stream at 310.

EXAMPLE 3 (FIGS. 1 and 4)

Example 2 is modified to the effect that the N-methylcarbamic acid chloride solution described in Example 2 as solution 302 is freed by distillation from free methylisocyanate 411 prior to the reaction with phenol, so that 523 g per hour of a 50% by weight solution of carbamic acid chloride in chlorobenzene, corresponding to 2.8 mol of carbamic acid chloride, are produced in the side stream 404 and 1495 g per hour of pure chlorobenzene are produced in the sump 403. The concentrated carbamic acid chloride solution 404 was mixed with 400 g of a circulated 80% by weight solution 405 of phenol in chlorobenzene, corresponding to 3.4 mol of phenol, and was converted into the carbamic acid aryl ester solution 406 or 106 to be split up with separation of hydrogen chloride 412. 172 g of a 90% by weight chlorobenzolic methyl isocyanate solution 108 or 408 and 664 g of a 50% by weight chlorobenzolic phenol solution 107 or 407 containing a further 1.9% by weight of unmodified carbamic acid phenyl ester are obtained per hour during the decomposition of this solution 106 or 406. The methyl-isocyanate solution 108 or 408 is introduced into the upper section of the distillation column D and there separated into pure product 411 and solvent in 404 and 403 respectively. A total of 222 g per hour, corresponding to a 97% yield of methyl-isocyanate, are obtained. The phenol solution 107 or 407 is concentrated in a separate distillation column by distilling off pure chlorobenzene 409 to an 80% by weight phenol content and fed back again into the phenol cycle 405. The chlorobenzene 409 produced in the process is fed back to the beginning of the process.

EXAMPLE 4 (FIGS. 1 and 2)

25 kg/h of a solution of N-ethylcarbamicacid phenylester solution in chlorobenzene obtained in analogy to Example 1 and freed from hydrogen chloride and excess phosgene containing 48% by weight (72.7 mols) of N-ethylcarbamicacid phenylester, 3% by weight of phenol and 0.3% by weight of diphenylcarbonate are split up in the vessel 101 at 190° C. to gaseous ethylisocyanate and gaseous phenol. The decomposition products enter the distillation column together with solvent vapors which distillation column is equipped with a dephlegmator the temperature of which is adjusted so that the temperature above the dephlegmator is 150° C. At the head of the column 5.56 kg/h of an 80% by weight solution of ethylisocyanate in chlorobenzene (108 or 208) are obtained which are separated in a further column (not shown in the drawing) into pure solvent and 4.45 kg/h of pure ethylisocyanate. Simultaneously 19.4 kg/h of a 34.2% by weight solution of phenol containing 8.5% by weight of N-ethylcarbamicacid phenylester are removed below the dephlegmator (107 or 207) and combined with the last mentioned pure solvent. The combined stream is recycled to column B. Simultaneously 15 l/h of a solution consisting essentially of solvent and small amounts of phenol are removed as a second side stream above the dephlegmator and recycled into the apparatus below the dephlegmator (not shown in the drawing).

EXAMPLE 5 (FIGS. 1 and 2)

25 kg/h of a solution in chlorobenzene containing 52% by weight (72.6 mol) of N-isopropylcarbamicacid phenylester, 2.5% by weight of phenol and 0.4% by weight of diphenylcarbonate obtained in analogy to Example 1 and freed from hydrogen chloride and excess phosgene are split in the splitting vessel (101) at 160° C. while—in contrast to the above examples where normal pressure was applied—a vacuum of 250 mbar is maintained. The decomposition products namely gaseous isopropylisocyanate and gaseous phenol and solvent vapors enter the distillation column which is equipped with a dephlegmator (104) the temperature of which is adjusted so that the temperature above the dephlegmator amounts to 120° C. At the head of the column 6.53 kg/h of a 75% by weight solution of isopropylisocyanate in chlorobenzene (108 or 208) are obtained which are separated in a further column (not shown in the drawing) in pure solvent and 4.9 kg/h of pure isopropylisocyanate. Simultaneously 18.4 kg/h of a 32.8% by weight solution of phenol in chlorobenzene which also contains 14.6% by weight of N-isopropylcarbamicacid phenylester are removed in a first side stream (107 or 207) underneath the dephlegmator and combined with the pure solvent mentioned hereinbefore. The combined streams are recycled to column B. Simultaneously 20 l/h of a second side stream consisting essentially of solvent and small amount of phenol are removed above the dephlegmator and recycled to the apparatus below the dephlegmator.

What is claimed is:

1. A process for the continuous production of monoisocyanates corresponding to the formula

in which
R represents an aliphatic hydrocarbon radical containing 1 to 3 carbon atoms, comprising thermally decomposing the corresponding N-alkylcarbamic acid aryl esters corresponding to the formula

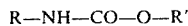

in which
R has the meaning above and
R' represents a radical of the type obtained by removing the hydroxyl group from a monophenol having a boiling point below 250° C. at normal pressure, and separating the decomposition products by decomposition, further characterized in that
(a) a solution of the N-alkylcarbamic acid aryl ester in an organic solvent, which solvent is inert under the reaction conditions and has a boiling point lying at least 20° C. above the boiling point of the monoisocyanate to be formed, is heated to a temperature of from 160° C. to 250° C. at normal pressure or at slightly reduced pressure within the range of 200 to 1013 mbar, thereby resulting in the decomposition of the ester into the corresponding monoisocyanate and the corresponding phenol, as well as the evaporation of the solvent and the decomposition products, and
(b) the vapors formed are fed into a distillation column with the monoisocyanate obtained at the head of the column and with the phenol and at least a major portion of the solvent obtained from a side stream or from several side streams.

2. The process of claim 1 wherein the aliphatic isocyanate may be olefinically unsaturated.

3. The process of claim 1, wherein the monoisocyanate obtained at the head of the column contains a portion of the solvent.

4. The process of claim 1, characterized in that a packed column having a temperature-controllable dephlegmator arranged above a side stream removal plate is used and wherein the temperature of the dephlegmator is selected in such a way that the total quantity of the phenol together with the major portion of the solvent are separated as a side stream below the dephlegmator and the monoisocyanate, optionally together with a portion of the solvent, is produced as head product.

5. The process of claim 1, characterized in that a temperature-controllable fractionating column having a dephlegmator which is arranged between two side stream removal plates is used and wherein the temperature of the dephlegmator is adjusted so that the main portion of the phenol can be removed in a first side stream below the dephlegmator and the monoisocyanate, optionally together with small amounts of solvent, can be removed at the head of the column whereby small amounts of phenol passing through the dephlegmator together with small amounts of isocyanate and carbamicacid arylester are removed as a second side stream above the dephlegmator as a solution in a part of the solvent which is recycled into the apparatus below the dephlegmator.

6. The process of claim 2, characterized in that the phenol produced as a side stream and the solvent produced as a side stream are reused, either as a mixture or after separation by fractional distillation, for the production of the solution used as starting material by dissolution of or reaction with gases which were formed during the gaseous phase phosgenation of monoamines corresponding to the formula R—NH$_2$, in which R has the meaning above.

* * * * *